US011311027B2

(12) United States Patent
Pearlman et al.

(10) Patent No.: US 11,311,027 B2
(45) Date of Patent: Apr. 26, 2022

(54) NUTRITIVE COMPOSITIONS AND METHODS RELATED THERETO

(71) Applicant: INV Nylon Chemicals Americas, LLC, Wilmington, DE (US)

(72) Inventors: Paul S. Pearlman, Redcar (GB); Hugo Federico Cueto Rojas, Redcar (GB); Gary Smith, Redcar (GB); Gregory S. Kirby, Redcar (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 72 days.

(21) Appl. No.: 16/176,389

(22) Filed: Oct. 31, 2018

(65) Prior Publication Data
US 2019/0124947 A1 May 2, 2019

Related U.S. Application Data

(60) Provisional application No. 62/579,507, filed on Oct. 31, 2017.

(51) Int. Cl.
| | |
|---|---|
| A23K 10/12 | (2016.01) |
| A23K 20/10 | (2016.01) |
| A23K 50/80 | (2016.01) |
| C12N 1/20 | (2006.01) |
| A23K 50/10 | (2016.01) |
| A23K 20/105 | (2016.01) |
| C12N 9/10 | (2006.01) |
| C12N 9/04 | (2006.01) |
| A23K 20/147 | (2016.01) |
| C12N 15/10 | (2006.01) |

(52) U.S. Cl.
CPC .............. *A23K 10/12* (2016.05); *A23K 20/10* (2016.05); *A23K 20/105* (2016.05); *A23K 20/147* (2016.05); *A23K 50/10* (2016.05); *A23K 50/80* (2016.05); *C12N 1/20* (2013.01); *C12N 9/0006* (2013.01); *C12N 9/1029* (2013.01); *C12N 15/102* (2013.01)

(58) Field of Classification Search
CPC ........ A23K 10/12; A23K 50/80; A23K 50/10; C12N 9/1029; C12N 9/0006; C12N 1/20; C12N 15/102
See application file for complete search history.

(56) References Cited

U.S. PATENT DOCUMENTS

| | | | |
|---|---|---|---|
| 6,207,217 | B1 | 3/2001 | Peoples et al. |
| 7,989,194 | B2 | 8/2011 | Seeger Pfeiffer et al. ................... 435/252.3 |
| 8,603,518 | B2 | 12/2013 | Boon et al. |
| 2008/0318302 | A1 | 12/2008 | Michael et al. ........... 435/252.3 |
| 2009/0114602 | A1 | 5/2009 | Logan et al. ................ 210/744 |
| 2011/0124063 | A1 | 5/2011 | Lynch |
| 2011/0127063 | A1 | 6/2011 | Chang ........................... 435/134 |
| 2013/0288323 | A1 | 10/2013 | Levin et al. .................. 435/146 |
| 2014/0330032 | A1* | 11/2014 | Lynch ....................... C12P 7/00 554/1 |
| 2015/0305369 | A1 | 10/2015 | Dake et al. ................ A23J 3/04 |
| 2017/0130211 | A1 | 5/2017 | Bradshaw et al. ... C12N 9/1217 |
| 2017/0240936 | A1 | 8/2017 | Smith et al. .......... C12P 13/001 |
| 2017/0298395 | A1 | 10/2017 | Tabita et al. |
| 2018/0002704 | A1 | 1/2018 | Chokkathukalam et al. ............... C12N 15/52 |
| 2018/0100160 | A1 | 4/2018 | Bawdon et al. |

FOREIGN PATENT DOCUMENTS

| | | |
|---|---|---|
| CN | 104762242 B | 10/2018 |
| JP | 2013179863 A | 9/2013 |
| WO | 2015/149147 A1 | 10/2015 |
| WO | WO 2015149147 A1 * | 10/2015 |
| WO | 2017165244 | 9/2017 |
| WO | WO 2017-165244 A1 * | 9/2017 |
| WO | 2018/106549 A1 | 6/2018 |

OTHER PUBLICATIONS

Raberg et al.A Closer Look on the Polyhydroxybutyrate-(PHB-) Negative Phenotype of Ralstonia eutropha PHB-4. PLOS one, 9(5):e95907, p. 1-11, 2014).*
Hanko et al. Characterization of a 3-hydroxypropionic acid-inducible system from Pseudomonas putida for orthogonal gene expression control in Escherichia coli and Cupriavidus necator. Scientific Reports, 7: 1724, p. 1-13, 2017).*
Balqis Binti AB. Ghani Metabolic engineering of Cupriavidus necator for the production of poly(3-hydroxybutyrate-co-3-hydroxyhexanoate), University Sains Malaysia, Ph.D. Dissertation, May 2017, p. i-xxiv, and p. 1-24.*
De Gelder et al. "Monitoring Poly(3-hydroxybutyrate) Production in Cupriavidus necator DSM 428 (H16) with Raman Spectroscopy" Anal. Chem. 2008 80-2155-2160.
Oburca et al. "Application of random mutagenesis to enhance production of polyhydroxyalkanoates by Cupriavidus necator H16 on waste frying oil" World Jorunal of Microbiology and Biotechnology 2013 29(1):2417-2428.
International Search Report and Written Opinion in PCT/US2018/058382 dated Jan. 25, 2019.
Schlegel et al., "The Isolation of Mutants Not Accumulating Poly-Beta-Hydroxybutyric Acid", Arch Mikrobiol. 1970, vol. 71, No. 3, 1970, pp. 283 294.
Kihlberg et al., "The Microbe as a Source of Food", Annual Review of Microbiology, vol. 26, 1972, pp. 427-466.
Sambrook et al., "Molecular Cloning: A Laboratory Manual", Cold Spring Harbor Laboratory Press, 3rd ed., vols. 1, 2 and 3, 2001, 3 pages.

(Continued)

*Primary Examiner* — Iqbal H Chowdhury (57) ABSTRACT

Nutritive compositions containing an organism having attenuated or no poly(3-hydroxybutyrate) production are provided. These nutritive compositions are useful as feed, such as animal feed and feed additives for ruminants, non-ruminants and aquaculture, etc. Materials and methods for production of these organisms are provided.

4 Claims, 3 Drawing Sheets

Specification includes a Sequence Listing.

(56) References Cited

OTHER PUBLICATIONS

Taniguchi et al., "Microbial Production of Poly(hydroxyalkanoate)s from Waste Edible Oils", Green Chemistry, Issue 5, Jul. 22, 2003, pp. 545-548.
Verlinden et al., "Production of Polyhydroxyalkanoates From Waste Frying Oil by Cupriavidus Necator", AMB Express, vol. 1 No. 11, Jun. 10, 2011, 8 pages.
Kunasundari et al., "Revisiting the Single Cell Protein Application of Cupriavidus necator H16 and Recovering Bioplastic Granules Simultaneously", PLoS ONE 8(10): e78528, Oct. 24, 2013, 14 pages.
Eggers et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, 2014, pp. 7702-7709.
Raberg et al., "A Closer Look on the Polyhydroxybutyrate-(PHB−) Negative Phenotype of Ralstonia eutropha PHB-4", Proteomic View on Mutant R. eutropha PHB-4, May 2, 2014, 11 pages.
Obruca et al., Utilization of Oil Extracted from Spent Coffee Grounds for Sustainable Production of Polyhydroxyalkanoates, Applied Microbiology and Biotechnology, vol. 98, Issue 13, 2014, pp. 5883-5890.
Nielsen et al., "Food Waste Conversion to Microbial Polyhydroxyalkanoates", Microbial Biotechnology, vol. 10, Issue 6, Jul. 24, 2017, 22 pages.
Estelle et al., "Isopropanol production with engineered Cupriavidus necator as bioproduction platform", Applied Microbiology and Biotechnology, vol. 98, No. 9, pp. 4277-4290, Mar. 7, 2014.
Extended Search Report received for EP Application No. 18873786.0, dated Aug. 5, 2021, 16 Pages.

\* cited by examiner

NUTRITIVE COMPOSITIONS AND METHODS RELATED THERETO

This patent application claims the benefit of priority from U.S. Provisional Application Ser. No. 62/579,507, filed Oct. 31, 2017, teachings of which are herein incorporated by reference in their entirety.

FIELD

Nutritive compositions containing an organism originally capable of poly(3-hydroxybutyrate)(PHB) production which has been modified to attenuate or eliminate PHB production are provided, which are useful as, for example, nutrition, feed and/or feed additives. Methods for production of these organisms for use in the nutritive compositions and feed and feed additives are provided.

BACKGROUND

Poly(hydroxyalkonates) (PHA) are accumulated in a large number of prokaryotes and serve as intracellular storage compounds for carbon and energy. Because of their thermoplastic and biodegradability, PHAs have various applications in industry and medicine.

For example, single cell protein (SCP), namely microbial cell material and organisms producing PHA intended to be used as food or feedstocks, has been considered for the last few decades. See, for example, Kihlberg, R. Annual Review of Microbiology 1972 26:427-466 and U.S. Pat. No. 6,207,217.

Single cell protein made from PHA-producing microorganisms such as *Cupriavidus necator*, previously known as *Ralstonia eutropha*, has been explored for a number of years as a component in animal feed (Egers, J. and Steinbuchel, A. Applied Environmental Microbiology 2014 80(24):7702-7709 and Raberg et al. PLOS ONE 2014 9(5):e95907).

However, such organisms have not been exploited as a feed because the most frequently found PHA polymer is poly(3-hydroxybutyrate) (PHB) which is rarely digestible and offers little to no nutritional value. The PHB component also reduces the protein content of the organism. In addition, non-nutritive PHB storage compound in the cytoplasm takes up physical space, leaving less space for nutritive compounds. Further, in some instances, the PHB components had a detrimental impact on biological functions, such as digestive system processes.

In recent work by Boon (U.S. Pat. No. 8,603,518) and Nonato (WO 2015149147), it was shown that adding PHB depolymerase enzymes to a feed mixture can result in an increase in the digestibility of the PHB. However, the total protein content for these feed mixtures is still reduced.

Kunasundari et al. (PLOS ONE 2013 8(10):e78528) discloses a biological recovery process of PHA which forms the basis for a combined synergetic feed and purification and separation process of PHA granules from lyophilized cells of *C. necator* H16.

WO2018/106549 discloses microorganisms and methods for producing PHB and protein for use in feed and nutritional supplement compositions.

There is a need for alternative methods for addressing the problem of PHBs in organism based nutritive compositions and feed mixtures.

SUMMARY

An aspect of the present invention relates to nutritive compositions comprising an organism originally capable of producing poly(3-hydroxybutyrate) (PHB) wherein the organism has attenuated and/or no PHB production.

In one nonlimiting embodiment, the organism of the nutritive composition does not comprise an exogenous nucleic acid. In one nonlimiting embodiment, the organism of the nutritive composition has at least one modification of one or more of the phaCAB operon enzymes excluding a phasin modification. In one nonlimiting embodiment, PHB production in the organism is attenuated or eliminated by eliminating or attenuating activity of one or more phaCAB operon enzymes excluding a phasin modification. In one nonlimiting embodiment, the organism of the nutritive composition is *Cupriavidus necator*. In one nonlimiting embodiment, the organism of the nutritive composition having attenuated PHB production produces undetectable PHB.

In one nonlimiting embodiment, the single cell protein of the nutritive composition has a higher concentration of amino acid(s), oligopeptides, polypeptides or derivatives thereof, as compared to a single cell protein of a nutritive composition not having this organism. In one nonlimiting embodiment, the nutritive composition has higher crude protein content as compared to a nutritive composition not having the organism. In one nonlimiting embodiment, crude protein in the organism is at least 40% to 70% of the organism mass.

Another aspect of the present invention relates to feed and feed additives comprising these nutritive compositions. In one nonlimiting embodiment, the nutritive composition is incorporated at a level of at least 10% to 30% by weight of the feed or feed additive.

Another aspect of the present invention relates to methods for producing organisms for these nutritive compositions and feed/feed additives. In these methods, a fermentation feedstock is inoculated with the organism having attenuated and/or no PHB production. In one nonlimiting embodiment, the organism of the nutritive composition does not comprise an exogenous nucleic acid. In one nonlimiting embodiment, the organism of the nutritive composition has at least one modification of one or more of the phaCAB operon enzymes excluding a phasin modification. In one nonlimiting embodiment, PHB production in the organism is attenuated or eliminated by eliminating or attenuating activity of one or more phaCAB operon enzymes excluding a phasin modification. In one nonlimiting embodiment, the organism of the nutritive composition is *Cupriavidus necator*. The inoculated organism is then cultured under conditions resulting in organism growth and/or multiplication followed by isolation or harvesting of the organism from the fermentation feedstock. Liquid or gas fermentation can be used. In one nonlimiting embodiment, conditions of mixotrophic fermentation are used. In one nonlimiting embodiment, the method further comprises incorporation of the isolated organism into a feed or feed additive.

Another aspect of the present invention relates to a method for improving survivability of a livestock or aquaculture animal by feeding the animal the feed or feed additive of this invention.

Another aspect of the present invention relates to a method for decreasing a waste-product or waste-products from commercial operations. In this method, an organism originally capable of producing poly(3-hydroxybutyrate) (PHB) wherein the organism has attenuated and/or no PHB production, is grown in the waste-product or waste-products. In one nonlimiting embodiment, the organism does not comprise an exogenous nucleic acid. In one nonlimiting embodiment, the organism has at least one modification of one or more of the phaCAB operon enzymes excluding a phasin modification. In one nonlimiting embodiment, the organism is *Cupriavidus necator*. The organism is then harvested and incorporated into a feed or feed additive.

Yet another aspect of the present invention relates to a method for producing a single cell protein. The method comprises selecting an organism capable of producing poly (3-hydroxybutyrate)(PHB) and eliminating or attenuating activity of one or more phaCAB operon enzymes excluding a phasin modification in the organism.

DETAILED DESCRIPTION

The present invention relates to nutritive compositions. Such nutritive compositions are suitable for use in, for example, feed and feed additives.

The terms "feed" or "feed composition" or "feed additive", as used herein, refer to any compound, preparation, mixture or composition suitable for, or intended for, intake by an animal.

The term "nutritive" or "nutritive composition", as used herein, denotes usefulness as a nutritional component, such as in feed, feed compositions or feed additives. The nutritive compositions can find use as a complete animal feed (diet) or as a supplement to animal feed.

The term "animal" includes all animals including human. Examples of animals are non-ruminants, and ruminants. Ruminant animals include, for example, animals such as sheep, goat, and cattle, e.g. cow such as beef cattle and dairy cows. The animal may also be a non-ruminant animal. Non-ruminant animals include pet animals, e.g. horses, cats and dogs; mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term "aquaculture", as used herein, refers to the rearing of aquatic animals as food.

Nutritive compositions of the present invention comprise an organism or SCP derived from an organism originally capable of producing poly(3-hydroxybutyrate) (PHB) which has attenuated and/or no PHB production. The organism with attenuated and/or no PHB production may be obtained via genetic engineering, by adaptive mutation, or by selective isolation of naturally occurring mutant strains that do not produce PHB. In one nonlimiting embodiment, the organism does not comprise an exogenous nucleic acid. Methods suitable for use with the present invention are described in, for example, Molecular Cloning: A Laboratory Manual, 3rd ed., Vols 1, 2 and 3, J. F. Sambrook and D. W. Russell, ed., Cold Spring Harbor Laboratory Press, 2001.

Nonlimiting examples of organisms originally capable of producing PHB for use in the nutritive compositions of the present invention include prokaryotes from the genera of Proteobacteria such as *Cupriavidus*, *Raistonia* and *Rhodobacter*. In one nonlimiting embodiment the organism is selected from *Cupriavidus necator* or *Rhodobacter sphaeroides*. In one nonlimiting embodiment, the organism is *Cupriavidus necator*.

In one nonlimiting embodiment, PHB production in the organism is attenuated or eliminated by modifying one or more of the phaCAB operon enzymes which enable the strain to produce PHB. In one nonlimiting embodiment, the organism is a ΔphaCAB H16 *C. necator* strain. In one nonlimiting embodiment, the organism is a PHB-strain. In one nonlimiting embodiment, the PHB-strain is produced by a G320A point mutation in phaC.

By phaCAB operon enzymes it is meant to include enzymes phaA, phaB, and phaC. In one nonlimiting embodiment, the organism has at least one modification of one or more of the phaCAB operon enzymes excluding a phasin modification. By "modify", "modifying" or "modification", as used herein it is meant to include gene deletion, gene substitution or gene insertion in one or more genes encoding phaA, phaB or phaC. Various methods for modification can be used.

In one nonlimiting embodiment, modification is carried out by allele exchange. In this embodiment, genome edits are made in an organism such as *C. necator* by allele exchange (also referred to as allelic exchange). In one nonlimiting embodiment, the organism is a ΔphaCAB H16 *C. necator* strain generated using allele exchange.

In one nonlimiting embodiment, modification is carried out by chemical mutagenesis. In one nonlimiting embodiment, a PHB-*C. necator* strain is generated through chemical mutagenesis. In one nonlimiting embodiment, chemical mutagenesis is used to produce a PHB-strain with a G320A point mutation in phaC.

Figure 1:
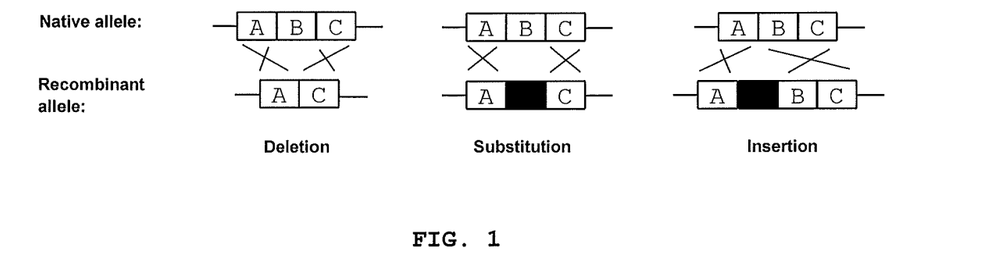
FIG. 1 is an illustration of recombinant allele configurations for making a deletion, substitution or insertion of DNA sequence in the genome of *C. necator*. An allele may be considered as having 3 parts; 'A', 'B' and 'C'. Provided the DNA sequence represented by 'A' and 'C' is identical between a recombinant allele and the native allele, the sequence represented by 'B' may be deleted (to generate a gene 'knock-out') or substituted (with the sequence represented by '01'). Alternatively, a non-native sequence (represented by '01') may be inserted between 'A' and 'B'."

The term 'allele' is often used interchangeably with the term 'gene' more generally, refers to a defined genomic locus. In allele exchange, a specific run of DNA sequence in an organism's genome (i.e., the native allele) is literally exchanged for a recombinant/mutant/synthetic run of DNA sequence (i.e., recombinant allele). Depending on the nature of the recombinant allele, this may result in a gene deletion, a gene substitution or a gene insertion (see FIG. 1).

In one nonlimiting embodiment, recombinant/synthetic alleles can be constructed via gene synthesis and/or standard molecular biology techniques. These are then cloned into a plasmid vector for transfer into the organism and execution of the allele exchange procedure. In one nonlimiting embodiment, the plasmid vector comprises DNA sequence including a positive selection gene that confers selective advantage to the organism, such as antibiotic resistance, and a negative or counter selection gene that eliminates or inhibits growth of the host organism upon selection such as thymidine kinase. These selection genes facilitate execution of the allele exchange procedure. At the end of the procedure, no part of the plasmid vector remains inside the host cell. Accordingly, while the modified allele is passed onto progeny cells, no part of the plasmid vector is passed on.

In one nonlimiting embodiment, the SCP of the nutritive composition has a higher concentration of amino acid(s), oligopeptides, polypeptides or derivatives thereof, as compared to a single cell protein of a nutritive composition not having this organism. Accordingly, use of the organism of the present invention can provide nutritive compositions with a higher concentration of amino acid(s), oligopeptides, polypeptides or derivatives thereof, as compared to a composition having an unmodified organism. Further, nutritive compositions similar in concentration to a composition having an unmodified organism can be prepared using less SCP or modified organism of the present invention.

In one nonlimiting embodiment, the organism used in the nutritive composition has a total amino acid level of greater than 40%. In another nonlimiting embodiment, the total amino acid level is greater than 50%. In another nonlimiting embodiment, the total amino acid level is greater than 60%. In another nonlimiting embodiment, the total amino acid level is greater than 70%. In another nonlimiting embodiment, the total amino acid level is greater than 75%. In yet another embodiment, the total amino acid level is greater than 80%.

In one nonlimiting embodiment, the organism of the present invention provides the nutritive compositions with a higher amount of total amino acids as compared to similar organisms that have not been modified. In another nonlimiting embodiment, less organism of the present invention can be used to provide nutritive compositions with similar total amino acid levels to compositions containing similar organisms that have not been modified.

In one nonlimiting embodiment, single cell protein of the present invention total amino acid levels are unexpectedly increased at least 10%, 20%, or even 30% more than would be expected with proportional reduction in PHB levels alone.

The modified organisms of the present invention exhibit a higher amount of protein as compared to unmodified organism. Accordingly, organisms of the present invention can provide the nutritive compositions with a higher amount of protein as compared to a composition having an unmodified organism. In one nonlimiting embodiment, crude protein level is increased at least 10%, 20, or even 30% more than would be expected just with the proportional reduction in PHB levels. In one nonlimiting embodiment, the organism used in the nutritive composition has a crude protein level of greater than 40% protein as estimated by total nitrogen. In another nonlimiting embodiment, the crude protein level is greater than 50% protein as estimated by total nitrogen. In another nonlimiting embodiment, the crude protein level is greater than 60% protein as estimated by total nitrogen. In another nonlimiting embodiment, the crude protein level is greater than 70% protein as estimated by total nitrogen. In another embodiment, the crude protein level is greater than 75% protein as estimated by total nitrogen. In yet another nonlimiting embodiment, the crude protein level is greater than 80% protein as estimated by total nitrogen. In one nonlimiting embodiment, the organism of the present invention provides the nutritive compositions with a higher amount of protein as compared to similar organisms that have not been modified. In another nonlimiting embodiment, less organism of the present invention can be used to provide nutritive compositions with similar protein levels to compositions containing similar organisms that have not been modified. There are a number of methods to measure total nitrogen in the organism. A nonlimiting example is the Kjeldahl method (see https with the extension people.umass.edu and the further extension of /~mcclemen/ 581Proteins.html of the world wide web) wherein the % nitrogen is multiplied by an N-factor to calculate crude protein content. While various N-factors may be used, in the present invention, an N factor of 6.25 was the multiplier.

The present invention also relates to a method for producing a SCP for use in these nutritive compositions. In one nonlimiting embodiment, the method comprises selecting an organism capable of producing poly(3-hydroxybutyrate) (PHB) and eliminating or attenuating activity of one or more phaCAB operon enzymes excluding a phasin modification in the organism. Without being bound to any theory, it is believed that maintaining a phasin operable embodiment provides biological advantages to the organism.

Various methods can be used to produce organisms for the nutritive compositions of the present invention.

In one nonlimiting embodiment, organism is produced via fermentation under conditions in which the organism grows and/or multiplies. For example, for an aerobic organism such as *Cupriavidus*, the organism may be cultured at room temperature in pH conditions of 6.4 to 6.8 with mixing either by agitation/mechanical means or by a loop or air-lift reactor. As will be understood by the skilled artisan upon reading this disclosure, however, such exemplary fermentation conditions are in no way limiting to this invention and alternative fermentations conditions routinely determined by the skilled artisan may be used for various organisms.

In one nonlimiting embodiment, the fermentation is conducted in a batch mode.

In one nonlimiting embodiment, the fermentation is conducted in fed batch mode.

In another nonlimiting embodiment, the fermentation is conducted in a continuous mode.

In one nonlimiting embodiment, organism is produced via liquid fermentation. In one nonlimiting embodiment, the liquid fermentation utilizes one or more feed components that are fermentable or metabolizable by the organism. Nonlimiting examples of feed components include sugars, glycerol, fructose, fatty acids, carboxylic acids, monosaccharides, disaccharides, lignocellulose, hemicellulose, cellulose, lignin, levulinic acid and formic acid, amino acids, proteins, triglycerides, agricultural waste, condensed distillers' solubles or municipal waste, alcohols and/or other soluble components as feedstock. In one nonlimiting embodiment, the feedstock for liquid fermentation is derived from lower value by-products or waste-products from commercial operations. In one nonlimiting embodiment, the feedstock for liquid fermentation is derived from ethanol thin stillage stream. In one nonlimiting embodiment, the feedstock for liquid fermentation is derived from cooking oil.

In another nonlimiting embodiment, organism is produced in a gas fermentation utilizing gaseous feedstock comprising one or more feed components that are fermentable or metabolizable by the organism. Examples of feed components include, but are not limited to, carbon monoxide, carbon dioxide, hydrogen, methane, syngas, ethane, or waste stream, or derivative thereof, of a chemical or petrochemical industry. In one aspect of the present invention, the organism was produced using gas fermentation, wherein said gas fermentation process comprises CO2/H2.

In yet another embodiment, organism is produced via mixotrophic fermentation where gaseous and non-gaseous feedstocks are co-fermented.

Nutritive compositions of the present invention produced from these organisms can then be added to animal feed or used as a feed itself.

In one nonlimiting embodiment, the cell membrane of the organism is broken down via lysis to improve the availability of the protein to the animal. Either mechanical or chemical lysis can be used.

In one nonlimiting embodiment, the organism is inactive, non-replicative or nonviable. In one nonlimiting embodiment this is achieved via pasteurization at, for example, 60° C. for 30 minutes. As will be understood by the skilled artisan upon reading this disclosure, however, alternative methods can be used.

In one nonlimiting embodiment, the nutritive composition is incorporated into the animal feed at greater than 10% by weight of the animal feed. In another nonlimiting embodiment, the nutritive composition is incorporated into the animal feed at greater than 20% by weight of the animal feed. In yet another nonlimiting embodiment, the nutritive composition is incorporated into the animal feed at greater than 30% by weight of the animal feed.

The animal feed may be used for feeding non-ruminants and ruminants. Ruminant animals include, for example, animals such as sheep, goats and cattle, e.g. cows such as beef cattle and dairy cows. The animal may also be a non-ruminant animal. Non-ruminant animals include pet animals, e.g. horses, cats and dogs; mono-gastric animals, e.g. pigs or swine (including, but not limited to, piglets, growing pigs, and sows); and poultry such as turkeys, ducks and chickens (including but not limited to broiler chicks, layers).

The animal feed may also be used in aquaculture for fish (including but not limited to salmon, trout, tilapia, catfish and carp); and crustaceans (including but not limited to shrimp and prawn), The following section provides further illustration of the methods and compositions of the present invention. These working examples are illustrative only and are not intended to limit the scope of the invention in any way.

EXAMPLES

Example 1

Three strains were grown under identical experimental conditions to compare their PHB levels. The three strains were *Cupriavidus necator* H16 wild-type, *Cupriavidus necator* H16 ΔphaCAB ΔA0006-9 (as described in published application US20180100160, which is hereby incorporated by reference in its entirety), and *Cupriavidus necator* H16 PHB4—(see Schlegel et al. Arch Mikrobiol 1970 71: 283-294). The three strains were grown at 30° C., 220 rpm and a starting pH of 6.6, in media 1 (see Table 1) for 24 hours. Optical density at 600 nm ($OD_{600}$) was measured and a suitable inoculum volume prepared to allow a starting $OD_{600}$ of 0.2 in the subsequent Ambr15F experiment (in short, a nitrogen limited fed batch cultivation designed to accumulate sufficient biomass for downstream amino acid analysis).

Eight vessels for each strain, were run on the Sartorius Ambr15f microfermentation system. An initial total volume of 7.7 ml (media 2 (see Table 1) and inclusive of the inoculum volume described above) was incubated at 30° C., 1500 rpm and a maintained target dissolved oxygen concentration (DO) of 10% (achieved and maintained through fixed agitation at 1500 rpm, and aeration from 0.1 ml/min to a potential of 60 ml/min as required). The pH was maintained at 6.6 via additions of 10% wv KOH and 10% vv $H_2SO_4$.

The cultures were allowed to accumulate in a batch mode of operation until initial nitrogen limitation was attained (observable as a spike in DO and confirmed later via ammonium assay) at which point a feed at a rate of 1.5μ/min was switched on for a period of 48 hours, feeding a total volume of 4.32 ml of media 3 (see Table 1).

After completion of growth, all 8 vessels for each strain were pooled into a single volume, pasteurised (65° C., 30 minutes), centrifuged (4000 rpm, 30 minutes) and the cell pellet retained. The cell pellet was freeze dried for 48 hours (−60° C. and 120 mTor) and sent for analysis.

TABLE 1

| Component | Media 1 g/L | Media 2 g/L | Media 3 g/L |
|---|---|---|---|
| Fructose | 12 | 19.15 | 141.89 |
| Nitrilotriacetic acid | 0.15 | 0.15 | 0.15 |
| $KH_2PO_4$ | 1.4 | 0.51 | 2.97 |
| $Na_2HPO_4$ | 0.94 | 0.34 | 1.98 |
| $(NH_4)_2SO_4$ | 3.365 | 3.37 | 19.63 |
| $MgSO_4 \cdot 7H_2O$ | 0.5 | 0.5 | 0.5 |
| $CaCl_2 \cdot 2H_2O$ | 0.01 | 0.01 | 0.01 |
| $NH_4$ (Fe-II)SO4 | 0.05 | 0.05 | 0.05 |
| Trace metal solution (see Table 12A) | 10 | 10 | 10 |
| Antifoam 204 | — | 0.5 | 0.5 |

Analysis of PHB levels was performed using LC-MS. Similar results were also obtained using other standard methods, such as GC-FID gas chromatography—flame ionization detector). The LC-MS parameters are as shown in Table 2.

TABLE 2

| Instrument | Agilent 6890 Series LC-MS System (ING 326) |
|---|---|
| Date Created | December 2017 |
| Date Modified | |
| Primary Analytes of Interest | 3-HBA (3-hydroxybutyric acid) and 3-HVA (3-hydroxyvaleric acid) in monomeric form |
| Injection Parameters | |
| Injection Type | Closed Loop (5 μL) |
| Injection Volume | 7 μL |
| Solvent Wash 1 | Solvent A |
| Solvent Wash 2 | Solvent B |
| LC Parameters | |
| Column Type | Kinetex ®2.6 pm HILIC 100 Å |
| Column Dimensions | 100 × 2.1 mm |
| Solvent Line A | 50:50 ACN/water with 10 mM ammonium formate |
| Solvent Line B | 90:10 ACN/water with 10 mM ammonium formate |
| Flow Rate | 0.3 mL min−1 |
| Expected Backpressure (t = 0) | 120 bar |
| Column Temperature | 35° C. |
| Solvent Composition | |
| Time | Solvent A | Solvent B |
| min | % | % |
| 0 | 10 | 90 |
| Isocratic run at 90% B, 6 min runtime | | |
| Detection | | |
| UV Wavelength | 210 nm |
| MS Drying Gas Flow | 5 L min−1 |
| MS Nebulizer | 45 psig |
| MS Drying Gas Temperature | 250° C. |
| MS Vaporiser Temperature | 200° C. |
| MS Stop Time | 15 |

TABLE 2-continued

| MS Signal | Time (min) | On/Off | Fragmentor | SIM | Polarity | Dwell (msec) |
|---|---|---|---|---|---|---|
| 1 | 1.0 | ON | 100 | 103.1 | negative | 140 |
| 2 | 1.0 | ON | 100 | 118.1 | negative | 140 |
| 3 | 1.0 | ON | 100 | 85.1 | negative | 140 |
| 4 | 1.0 | ON | 100 | Full scan | negative | 140 |

| Analyte | RT (min) | Channel | LOD (µg L−1) |
|---|---|---|---|
| 3-HBA monomer | 2.8 | 1 | 0.1 |

Analysis shows that the *Cupriavidus necator* H16 ΔphaCAB ΔA0006-9 and *Cupriavidus necator* H16 PHB4-strains were deficient in polyhydroxybutyrate (PHB) accumulation. Slides were prepared by melting 1% agarose in water, adding 100 µl of hot agarose to the slide, placing a coverslip on top of the agarose to spread it to a thin layer and letting the agarose solidify. Cellular PHB was stained using Nile Red using a protocol adapted from bio-protocol with the extension.org/e2748 of the world wide web. 1 ml overnight culture at 12400 rpm for 2 min were spun down and resuspended in ~50 µl supernatant or water. 4 µl of cell suspension was added to 1 µl of Nile Red (10 µg/ml). The coverslip on the agarose pad on the slide was removed and 1.5 µl of the stained cell suspension added to the agarose pad. A new coverslip was placed over the cells and the cells were observed under the microscope at 100× with DsRed filter.

Figure 3A:
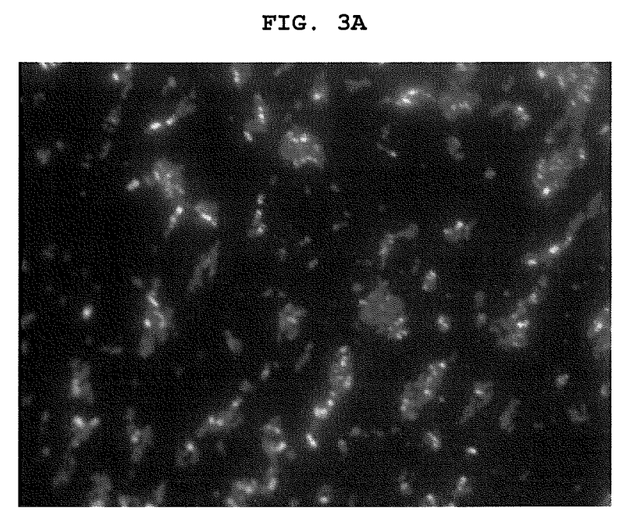
FIGS. 3A, 3B and 3C show polyhydroxybutyrate (PHB) accumulation in the *Cupriavidus necator* H16 wild-type cells (FIG. 3A) and no polyhydroxybutyrate (PHB) accumulation in the *Cupriavidus necator* H16 ΔphaCAB (FIG. 3B) and *Cupriavidus necator* H16 PHB4-strains (FIG. 3C).
Figure 3B:
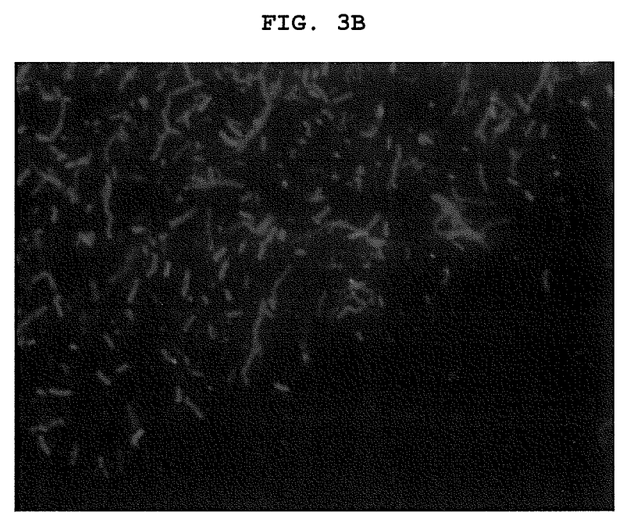
Figure 3C:
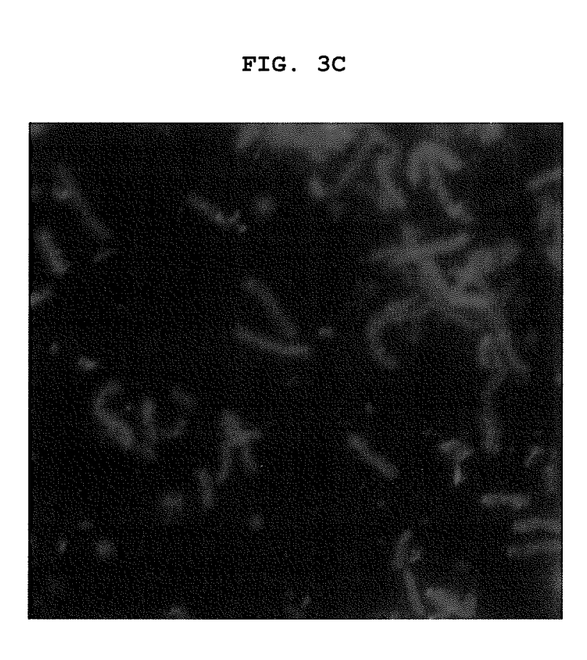

Results are shown in Table 3 as well as FIGS. 3A, 3B and 3C.

TABLE 3

| Sample number | *Cupriavidus necator* H16 wild-type wt/wt* | *Cupriavidus necator* H16 ΔphaCAB ΔA0006-9 wt/wt* | *Cupriavidus necator* H16 PHB4-. wt/wt* |
|---|---|---|---|
| 1 | 46.4 | 0 | 0 |
| 2 | 47.3 | 0 | 0 |

% wtPHB:% wt dry cell wt

Amino Acid numbers were analyzed by Amino Acid Analysis Service Laboratory Inc. Boring, Oreg., USA and are depicted in Table 4.

TABLE 4

| AMINO ACID | Wild Type mg aa per gm prod. | Wild Type Relative Percent Amino Acid in Total Amino Acids | PHB− mg aa per gm prod. | PHB− Relative Percent Amino Acid in Total Amino Acids | Delta CAB mg aa per gm prod. | Delta CAB Relative Percent Amino Acid in Total Amino Acids |
|---|---|---|---|---|---|---|
| CYS02 (C) | 3.2 | 1.1% | 5.8 | 1.1% | 5.9 | 1.1% |
| HYP (Z) | 0.0 | 0.0% | 0.0 | 0.0% | 0.0 | 0.0% |
| ASP (D) | 27.8 | 9.8% | 52.8 | 9.8% | 51.3 | 9.8% |
| THR (T) | 15.3 | 5.4% | 28.3 | 5.2% | 27.5 | 5.3% |
| SER (S) | 11.8 | 4.1% | 22.5 | 4.2% | 21.9 | 4.2% |
| GLU (E) | 33.7 | 11.8% | 62.5 | 11.6% | 60.1 | 11.5% |
| PRO (P) | 10.4 | 3.7% | 21.4 | 4.0% | 20.7 | 3.9% |
| GLY (G) | 15.9 | 5.6% | 31.0 | 5.7% | 30.1 | 5.8% |
| ALA (A) | 29.8 | 10.5% | 55.4 | 10.3% | 54.5 | 10.4% |
| VAL (V) | 19.8 | 6.9% | 36.7 | 6.8% | 35.7 | 6.8% |
| MET (M) | 7.7 | 2.7% | 18.3 | 3.4% | 17.8 | 3.4% |
| ILE (I) | 11.7 | 4.1% | 22.8 | 4.2% | 22.1 | 4.2% |
| LEU (L) | 26.1 | 9.2% | 50.1 | 9.3% | 48.6 | 9.3% |
| NLE | 0.0 | 0.0% | 0.0 | 0.0% | 0.0 | 0.0% |
| TYR (Y) | 11.6 | 4.1% | 21.3 | 4.0% | 20.7 | 3.9% |
| PHE (F) | 15.0 | 5.3% | 26.6 | 4.9% | 26.0 | 5.0% |
| HIS (H) | 5.9 | 2.1% | 11.6 | 2.2% | 11.3 | 2.2% |
| Tryptophan | 0.0 | 0.0% | 0.0 | 0.0% | 0.0 | 0.0% |
| LYS (K) | 16.97 | 6.0% | 31.38 | 5.8% | 30.08 | 5.7% |
| ARG (R) | 21.8 | 7.7% | 41.2 | 7.6% | 39.8 | 7.6% |
|  | 284.4 |  | 539.7 |  | 524.0 |  |
| Total percent Amino Acids (wt %) | 28.40% |  | 54.00% |  | 52.40% |  |

Example 2: Wild Type *Cupriavidus necator* H16

A strain of wild type *Cupriavidus necator* H16 was grown in a total of 6, 1 L continuously stirrer tank reactors (CSTR) in a continuous mode of operator. The wild type *Cupriavidus necator* H16 was grown at 30° C., 220 rpm and a starting pH of 6.6, in media 1 (see Table 5) for 24 hours. Optical density at 600 nm ($OD_{600}$) was measured and a suitable inoculum volume prepared to allow a starting $OD_{600}$ of 0.2 in the subsequent 1 L experiments (in short nitrogen limited continuous cultivations designed to accumulate enough biomass for downstream analysis).

Six vessels were run, each with a total volume of 0.8 L (media 2 (see Table 5) and inclusive of the inoculum volume described above) and incubated at 30° C., 500 rpm and a maintained target dissolved oxygen concentration (DO) of 30% (achieved and maintained through cascade of agitation up to 1500 rpm, and fixed aeration of 0.15 vvm). The pH was maintained at 6.6 via additions of 10% wv KOH and 10% vv $H_2SO_4$. The cultures were grown in batch until fructose limitation was attained (observable as a spike in DO) at which point two feeds, each at a rate of 20 g/h were switched on (media 3 and 4—see Table 5). A bleed was also switched on, the pump rate linked to a balance set to maintain a net weight of 0.8 Kg (note that the balance was calibrated to only consider the weight of the initial medium). Collectively at 40 g/h feed, a dilution rate of 0.05 $h^{-1}$ was achieved. Culture waste, derived from the bleed line, was harvested daily (approx. 960 g/day/vessel) and combined.

TABLE 5

| Component | Media 1 g/L | Media 2 g/L | Media 3 g/L | Media 4 g/L |
| --- | --- | --- | --- | --- |
| Fructose | 12 | 13.83 | — | 160 |
| Nitrilotriacetic acid | 0.15 | 0.15 | 0.3 | — |
| $KH_2PO_4$ | 1.4 | 0.55 | 4.24 | — |
| $Na_2HPO_4$ | 0.94 | 0.37 | 2.82 | — |
| $(NH_4)_2SO_4$ | 3.365 | 3.37 | 28 | — |
| $MgSO_4 \cdot 7H_2O$ | 0.5 | 0.5 | 1 | — |
| $CaCl_2 \cdot 2H_2O$ | 0.01 | 0.01 | 0.02 | — |
| $NH_4$ (Fe-II)SO4 | 0.05 | 0.05 | 0.1 | — |
| Trace metal solution (see Table 12A) | 10 | 10 | 20 | — |
| Antifoam 204 | — | 0.5 | 1 | — |

The cells were pasteurised (65° C., 30 minutes), centrifuged (4000 rpm, 30 minutes) and the cell pellet retained. The cell pellet was freeze dried for 48-96 hours (−60° C. and 120 mTor) and blended with the pellets from previous days until a net, dried cell biomass of >1.5 Kg was obtained. Upon blending, a small fraction of the resultant biomass was sent for analysis. Samples for protein analysis and amino acid profiling were collected and analysed to give the relative % weight amino acids, AA (% WT of amino acid/% WT of total amino acid) amino acids on a dry weight basis. Samples were analysed at the Experiment Station Chemical Laboratories at University of Missouri, Columbus, Mo. according to Code 0002 for the Amino Acid Profile and Code 0054 for the Crude Protein/Total Nitrogen (Kjeldahl).

The amino acid levels were compared with the amino acid levels for the *Cupriavidus necator* H16 ΔphaCAB strains grown and analysed using continuous fermentation with fructose. Results are shown in Table 6. Results indicate higher total amino acids in the *Cupriavidus necator* H16 ΔphaCAB strains compared to wild type *Cupriavidus necator* H16.

TABLE 6

| | Units | |
| --- | --- | --- |
| | % WT of AA/ % WT of total AA | % WT of AA/ % WT of total AA |
| | Strain | |
| | *Cupriavidus necator* H16 ΔphaCAB | wild type *Cupriavidus necator* H16 |
| | Feedstock | |
| | Fructose | Fructose |
| | Process | |
| | Continuous | Continuous |
| Alanine | 9.60 | 9.48 |
| Arginine | 7.70 | 7.65 |
| Aspartic Acid | 9.64 | 9.29 |
| Cysteine | 0.90 | 0.73 |
| Glutamic Acid | 11.95 | 11.35 |
| Glycine | 6.28 | 5.82 |
| Histidine | 2.18 | 2.60 |
| Hydroxylysine | 0.03 | 0.38 |
| Hydroxyproline | 0.04 | 0.00 |
| Isoleucine | 4.65 | 4.71 |
| Lanthionine | 0.00 | 0.00 |
| Leucine | 8.70 | 8.88 |
| Lysine | 6.32 | 6.77 |
| Methionine | 2.60 | 2.53 |
| Ornithine | 0.05 | 0.17 |
| Phenylalanine | 4.58 | 5.04 |
| Proline | 4.20 | 4.62 |
| Serine | 3.40 | 3.15 |
| Taurine | 0.05 | 0.17 |
| Threonine | 4.79 | 4.78 |
| Tryptophan | 1.63 | 0.83 |
| Tyrosine | 3.47 | 3.86 |
| Valine | 7.23 | 7.20 |
| Total Amino Acids (WT %) | 73.54 | 57.78 |
| Crude Protein* | 88.58 | 67.68 |
| PHB levels | 0% | 7% |

W/W % = grams per 100 grams of sample.
Results are expressed on a dry weight basis.
*Kjeldahl crude protein = (% N) × 6.25

Example 3: Generation of H16 ΔphaCAB *Cupriavidus necator*

The ΔphaCAB H16 *C. necator* strain was generated as follows using allele exchange. An allele exchange cassette with 500-1000 bp homology arms was constructed by PCR or DNA synthesis and cloned into p(TcColEloriTsacB), between oriT and sacB cassettes, by Gibson, CPEC or PvuI restriction digest. The integrity of the insert was confirmed by Sanger sequencing using primers BDIPRIM0591 (atcgaagagaagcaggacga (SEQ ID NO:1)) and BDIPRIM0589 (aacggcaggtatatgtgatgg (SEQ ID NO:2)). The plasmid was transferred into *E. coli* by electroporation and then into *C. necator* by conjugation. *C. necator* transconjugants/single cross-over integrants were selected on defined/minimal medium supplemented with appropriate antibiotic. The plates at were incubated and then inspected for single cross-over integrant colonies after several days incubation.

A number of clones were picked and re-streaked to purity. Individual clones were then picked into 1 ml TSB medium, without antibiotic selection and cultured to allow the second recombination event to occur. Aliquots of culture were then plated and double cross-over clones were selected. Recombinant clones were subsequently identified and confirmed by PCR, Sanger sequencing and appropriate phenotypic tests.

Example 4: Amino Acid Content of Single-Cell Protein of *Cupriavidus necator* Prepared from Clarified Ethanol Thin Stillage 1 mL of ΔphaCAB H16 *C. necator* strain was inoculated into 25 mL of clarified ethanol thin stillage diluted 1:4, incubated in a 50 mL flask at 30° C. and 200 rpm for 24 h. The ethanol thin stillage comprised lactic acid 2.61 g/kg; acetic acid 0.41 g/kg; glucose 0.73 g/kg; and glycerol 18.3 g/kg.

Subsequently, 20 mL from this 50 mL flask was inoculated into 280 mL of ethanol thin stillage diluted 1:4 and incubated in a 1 L flask at 37° C. and 200 rpm for 24 h. The total 300 mL of this second flask was used to inoculate 2.7 kg of filter sterilized syrup (dilution 1:4) in fermenter.

A batch fermentation process was run using the operational conditions and phases set out in Table 7. To control the bioreactor pH, the pH was maintained with both acid and base control of constant pH from the beginning of the process (pH 6.6±0.05). For pH control, sterilized (0.2 μm) solutions of KOH 1 mol/kg and $H_2SO_4$ 10% (w/w) (acid) were used.

TABLE 7

| Parameter | Batch phase |
|---|---|
| Temperature | 37° C. |
| Agitation, under cascade to control DO | 500 rpm to 800 rpm |
| pH | 6.6 |
| Total Mass (including inoculum) | 3 kg |
| DO controller set-point | ≥20% sat |
| Air flow rate (F_AIR) | 0.4 SLPM |
| Duration | 54 h |

A parallel bioreactor was run using a H16 *C. necator* wild type strain under the same conditions.

Following the fermentation process, the contents of the bioreactor were centrifuged and the pellet harvested. The amino acid and protein levels in the pellet were analysed using the standard amino acid analysis protocol well known European Pharmacopoeia (Ph. Eur.). The analysis results are shown in Table 8. In this Table, F of the Sample ID refers to the number of the fermenter while T refers to the number of hours between inoculation of the fermenter and the harvesting of the sample for analysis.

TABLE 8

| | Sample ID | | |
|---|---|---|---|
| | H16 ΔCAB - F3-T51 Cell Pellet (Washed) | H16 ΔCAB - F4-T51 Cell Pellet (Washed) | H16 "Wild Type"-F1-T50 Cell Pellet (Washed) |
| | FHR Sample ID | | |
| | 2 Average (n = 3) wt/wt % | 4 Average (n = 3) wt/wt % | 6 Average (n = 3) wt/wt % |
| Asparagine[1] | 9.4% | 9.2% | 9.3% |
| Glutamine[1] | 12.7% | 12.4% | 11.9% |
| Serine | 3.8% | 3.9% | 3.8% |
| Histidine | 1.8% | 1.9% | 1.7% |
| Glycine | 6.1% | 6.2% | 5.6% |
| Threonine | 5.1% | 5.1% | 5.2% |
| Arginine | 8.6% | 8.9% | 8.3% |
| Alanine | 10.7% | 10.7% | 10.6% |
| Tyrosine | 5.1% | 5.3% | 5.5% |
| Cystine/Cystene[3] | 0.1% | 0.1% | 0.1% |
| Valine | 8.5% | 8.3% | 8.2% |
| Methionine[3] | 2.9% | 3.0% | 2.7% |
| Tryptophan[2] | 1.3% | 0.7% | 2.4% |
| Phenylalanine | 4.8% | 4.9% | 5.0% |
| Isoleucine | 4.0% | 3.9% | 3.7% |
| Leucine | 8.6% | 8.8% | 8.6% |
| Lysine | 6.0% | 6.2% | 6.6% |
| Hydroxyproline | 0.9% | 0.8% | 0.7% |
| Proline | NA | NA | NA |
| Total | 100.4% | 100.2% | 100.0% |
| % Protein (Dry Basis) | 59.0% | 55.2% | 33.0% |
| Protein By Comb. (%) | 84.5% | 81.3% | 55.6% |

[1]Asparagine and Glutamine are converted to Aspartic acid and Glutamic acid during hydrolysis
[2]Hydrolysis by EP 2.2.56 Modified Method 3
[3]Hydrolysis by EP 2.2.56 Modified Method 1
(4) NA = Not included in Analysis

Example 5: Large-Scale Production of Single-Cell Protein of *Cupriavidus necator* for Fish Trials from Synthetic Clarified Thin Stillage The strain of H16 ΔphaCAB *Cupriavidus necator*, as described in Example 3, was adapted to grow in glycerol by sub-culturing in minimal medium with 8 g/L glycerol.

A two-step seed train was used to scale-up the growth of the strain before inoculating a 50-L fermenter containing synthetic thin stillage. The composition of the synthetic thin stillage is: glycerol 18.3 g/kg, sodium acetate 0.5575 g/kg, glucose 0.7275 g/kg, lactic acid (86.7%) 2.5 mL/kg, yeast extract 12.5 g/kg, $KH_2PO_4$ 3.25 g/kg, $NgSO_4.7H_2O$ 1.25 g/kg, ferric ammonium citrate 11.25 mg/kg, and antifoam 204 0.1 mL/kg. The synthetic thin stillage was prepared as follows: the following components were fully dissolved (in order) in de-ionized water: glycerol, sodium acetate, glucose, lactic acid in 70% of the final volume. Once all components were fully dissolved, $KH_2PO_4$, $MgSO_4.7H_2O$ and ferric ammonium citrate were added, and the volume of the solution brought to 90%, whilst making sure all the components were dissolved. Antifoam was added, and the pH adjusted with $NH_3$ 10% w/w and $H_2SO_4$ 10% v/v to 6.60±0.05. The volume of the solution was brought to 100% of the final volume and the solution was filter-sterilized using 0.2 μm filters.

49-L of the synthetic thin stillage were filter-sterilized into a 50-L working volume fermenter; the natural pH of the medium is close to 4.5, pH adjustment was performed inside the tank (final pH=6.6±0.1), with filter-sterilized $NH_3$ 10% w/w and $H_2SO_4$ 10% v/v. The full content of two 2.8-L Fernbach flasks was transferred into the fermenter as inoculum, to final working volume of 50-L. The initial cell density was designed to be 0.2 AU/mL<$OD_{600}$<0.5 AU/mL.

The pH of the fermentation was controlled at 6.6±0.1, with filter-sterilized $NH_3$ 10% w/w and $H_2SO_4$ 10% v/v. The $pO_2$ was controlled above 15% sat, being 100% DOsat the dissolved oxygen concentration at equilibrium with air at 1 bar (absolute pressure). Typically, the fermentation ends after 36 h of operation if the initial $OD_{600}$~0.5. The critical process parameter was cell density with a target of >8 gCDW/kg ($OD_{600}$~20 AU/mL). Other process parameters that must be met at the end of the batch are: % DO>90% sat, and glycerol conversion>95%. Once these parameters were achieved, the culture was used to seed the main fermenter.

The 50-L vessel in turn was the seed of two 750-L fermenters. 750-L of production medium were filter-sterilized into each 750-L fermenter; the natural pH of the medium is close to 4.5, pH adjustment was performed inside the tank, with a final pH=6.6±0.1. 25-L of the 50-L fermenter were used as seed, and transferred to the 750-L fermenters for a total working volume of 775 L.

The initial cell density was designed to be $OD_{600}$-0.8 AU/mL, with an approximate batch length around 36 h. Similar as above, the critical process parameter was cell density, with a target >8 gCDW/kg ($OD_{600}$-20 AU/mL). The pH of the fermentation was controlled at 6.6±0.1, with filter-sterilized $NH_3$ 10% w/w and $H_2SO_4$ 10% v/v. The $pO_2$ was controlled above 15% sat, being 100% DOsat the dissolved oxygen concentration at equilibrium with air at 1 bar (absolute pressure).

The batches from the two 750-L fermenters were mixed together and centrifuged. The concentrated solids were pasteurized to provide a biologically-inactive biomass.

Cell pellets were then freeze-dried and packaged and then used for fish trials. According to this Example, 15 kg of cell pellets were made.

Example 6: *Cupriavidus necator* H16 ΔphaCAB Single Cell Protein (SCP) Fish Feed Evaluation Consumption of the *Cupriavidus necator* H16 ΔphaCAB single cell protein and accessibility of amino acids and rate of was assessed in fish. As carnivorous fish (i.e. salmon) have the highest protein conversion rates, require the highest protein diets and are very selective with their food sources, a 28-day Atlantic salmon feed digestibility test was carried out. 15 kg of pasteurized freeze-dried *Cupriavidus necator* H16 ΔphaCAB Single Cell Protein (SCP) was prepared as described in Example 5.

In this digestibility test, 12 tanks of fish, each tank containing 25 salmon, were divided into 3 groups of 4 tanks. Each tank in the 3 groups of salmon was fed one of 4 diets with different % content of *Cupriavidus necator* H16 ΔphaCAB SCP (Reference diet, 10% SCP, 20% SCP, and 30% SCP) and their weight increase and amount of feed digested measured. The weight of each salmon at the start of the trial was 50 g and this increased to approximately 100 g by the end of the trial. In addition, faeces were collected to determine the portion digested of each amino acid in the feed fed to the fish. The following data were collected: water temperature, dissolved oxygen, mortality (if any), mean initial and final body weight of fish, daily feed intake, weight of faeces. Feeding behaviour and feed acceptability was monitored to ensure salmon adapted to their new diet.

Based on the 28-day digestibility study, the *Cupriavidus necator* H16 ΔphaCAB SCP (prepared according to Example 5 using synthetic thin stillage feed as feedstock) was well digested by the salmon showing higher growth than the Reference diet and excellent amino acid digestion.

The *Cupriavidus necator* H16 ΔphaCAB SCP not only contained elevated levels of protein compared to the Reference diet, but also demonstrated its protein and amino acids to be of superior quality based on feed intake (FI) and FCR results (see Table 9). There was an inverse relationship between *Cupriavidus necator* H16 ΔphaCAB SCP dietary inclusion and FI and FCR. The FI and FCR values decreased significantly as the inclusion level of SCP increased.

Survival of fish was 100% and indicated that *Cupriavidus necator* H16 ΔphaCAB SCP was a safe ingredient for Atlantic salmon.

TABLE 9

Initial (IBW - Day 0) and final (FBW - Day 28) body weight, weight gain (WG), thermal-unit growth coefficient (TGC), feed intake (FI) and feed conversion ratio (FCR) of Atlantic salmon fed diets with SCP (*Cupriavidus necator* H16 ΔphaCAB). Data are means (standard errors); means in a column with no superscript in common differ significantly based on the Tukey test (the absence of absence of superscript indicates no difference).

| Diet | IBW (g/fish) | FBW (g/fish) | WG (g/fish) | TGC | FI (g/fish) | FCR |
|---|---|---|---|---|---|---|
| A (Reference) | 47.2(0.8) | 85.1(1.1) | 37.9(0.6) | 0.195(0.003) | 28.7$(0.5)^a$ | 0.76$(0.00)^a$ |
| B (10% SCP) | 48.1(0.6) | 86.3(1.1) | 38.3(1.0) | 0.195(0.004) | 27.6$(0.8)^{ab}$ | 0.72$(0.00)^b$ |
| C (20% SCP) | 47.0(0.8) | 84.1(1.0) | 37.1(0.6) | 0.192(0.002) | 25.4$(0.4)^{bc}$ | 0.69$(0.00)^c$ |
| D (30% SCP) | 47.3(0.3) | 84.2(0.8) | 36.9(0.5) | 0.191(0.002) | 24.4$(0.2)^c$ | 0.66$(0.01)^c$ |

*Cupriavidus necator* H16 ΔphaCAB SCP inclusion did not affect protein digestibility, with no difference observed between the four experimental diets, as shown in Table 10. Both lipid and gross energy digestibility increased at ≥20% SCP inclusion level.

TABLE 10

Apparent digestibility coefficients (ADCs) of dry matter (DM), protein (P), lipid (L) and gross energy (GE) in diets of Atlantic salmon fed diets with SCP (*Cupriavidus necator* H16 ΔphaCAB).

| | ADC (% dry matter) | | | |
|---|---|---|---|---|
| Diet | DM | P | L | GE |
| A (Reference) | 90.1$(0.7)^c$ | 90.6(0.4) | 90.8$(1.4)^c$ | 80.1$(0.6)^c$ |
| B (10% SCP) | 90.7$(0.6)^{bc}$ | 90.2(0.4) | 92.3$(0.5)^{bc}$ | 80.8$(0.3)^{bc}$ |
| C (20% SCP) | 91.9$(0.7)^{ab}$ | 90.4(0.2) | 93.3$(1.0)^{ab}$ | 82.0$(0.5)^b$ |
| D (30% SCP) | 93.5$(0.8)^a$ | 90.9(0.5) | 95.6$(0.6)^a$ | 83.5$(0.6)^a$ |

Data are means (standard errors); means in a column with no superscript in common differ significantly based on the Tukey test (the absence of superscript indicates no difference).

The digestibility of the ten essential amino acids stayed at or near 90% across all four experimental diets (Table 10).

Therefore, *Cupriavidus necator* H16 ΔphaCAB SCP did not affect the availability of amino acids, regardless of its inclusion level. Although statistically different digestibility values were obtained, the differences were marginal and most likely due to the imprecision of the amino acid analytical method and typical experimental errors associated with digestibility method. The narrow standard errors indicated the results were highly consistent between replicates.

Fish feed formulation used in this test are depicted in Table 11.

TABLE 11

| Code | Ingredient | A (Reference) | B (10) | C (20) | D (30) |
|---|---|---|---|---|---|
| 55 | Dicalcium phosphate (40% $P_2O_5$) | 3.165 | 2.849 | 2.532 | 2.216 |
| 59 | Biolys | 0.563 | 0.506 | 0.450 | 0.394 |
| 60 | DL Methionine | 0.126 | 0.113 | 0.101 | 0.088 |
| 300 | Fish oil herring | 15.000 | 13.5000 | 12.000 | 10.500 |
| 320 | Vit & Min Premix | 0.300 | 0.270 | 0.240 | 0.210 |
| 500 | Fishmeal herring | 20.000 | 18.000 | 16.000 | 14.000 |
| 510 | Poultry meal (pet food grade) | 12.136 | 10.922 | 9.709 | 8.495 |
| 515 | Blood meal (Spray-dried) | 7.000 | 6.300 | 5.600 | 4.900 |
| 550 | Soy protein concentrate | 5.000 | 4.500 | 4.000 | 3.500 |
| 561 | Corn protein concentrate | 10.000 | 9.000 | 8.000 | 7.000 |
| 565 | Wheat gluten meal | 7.845 | 7.061 | 6.276 | 5.492 |
| 567 | Wheat flour | 18.365 | 16.479 | 14.592 | 12.706 |
|  | Single cell protein | 0.000 | 10.000 | 20.000 | 30.000 |
|  | Titanium Dioxide ($TiO_2$) | 0.500 | 0.500 | 0.500 | 0.500 |

| Code | Nutrient | Content | Unit |
|---|---|---|---|
| 1 | Volume | 100.000 | % |
| 2 | Dry Matter | 91.838 | % |
| 3 | Crude lipid | 20.000 | % |
| 5 | Crude protein | 48.000 | % |
| 6 | Crude fiber | 0.799 | % |
| 7 | Ash | 6.205 | % |
| 11 | Calcium | 1.255 | % |
| 12 | Phosphorus | 1.065 | % |
| 13 | Digestible phosphorus | 0.670 | % |
| 74 | Leucine | 4.341 | % |
| 75 | Isoleucine | 1.914 | % |
| 77 | Phenylalanine | 2.177 | % |
| 84 | Histidine | 1.262 | % |
| 85 | Arginine | 2.440 | % |
| 800 | Digestible lysine | 3.000 | % |
| 801 | Digestible methionine | 1.000 | % |
| 802 | Lysine | 3.480 | % |
| 803 | Methionine | 1.158 | % |
| 820 | Gross energy | 23.563 | MJ/kg |
| 821 | Digestible energy | 20.193 | MJ/kg |
| 830 | Astaxanthin | 0.000 | % |
| 840 | DHA | 0.725 | % |
| 841 | EPA | 1.015 | % |

Example 7: Biomass Production Using Continuous Mode Fermentation with Glycerol as Feedstock 200 µL of concentrated cells from *Cupriavidus necator* H16 ΔphaCAB adapted to grow in glycerol were used to inoculate 10 mL of inoculum culture medium (see Table 12) plus glycerol at 18 g $L^{-1}$ in 50 mL sterile tubes and incubated at 30° C., 220 rpm for 24 h. This culture was used to inoculate different tubes with 10 mL of fresh medium with glycerol with an initial OD600 of 0.2 AU/mL. The tubes were incubated at 30° C., 220 rpm for 24 h to an approximate OD600 of 2 AU/mL. 2×100 mL of these were monoseptically transferred into 1 L inoculum flasks ready for inoculation.

TABLE 12

Inoculum Culture media (filter sterilized 0.2 µm)

| Component | Concentration | Unit |
| --- | --- | --- |
| Nitrilotriacetic acid | 0.15 | g $L^{-1}$ |
| KH2PO4 | 1.4 | g $L^{-1}$ |
| Na2HPO4 | 0.94 | g $L^{-1}$ |
| (NH4)2SO4 | 3.365 | g $L^{-1}$ |
| MgSO4•7H2O | 0.5 | g $L^{-1}$ |
| CaCl2•2H2O | 0.01 | g $L^{-1}$ |
| NH4 (Fe-II)SO4•6H2O | 0.05 | g $L^{-1}$ |
| Trace metal solution (see Table 12A) | 10 | mL $L^{-1}$ |

TABLE 12A

Stock trace metal solution

| Component | Concentration | Unit |
| --- | --- | --- |
| ZnSO$_4$•7H$_2$O | 0.100 | g $L^{-1}$ |
| MnCl$_2$•4H$_2$O | 0.030 | g $L^{-1}$ |
| H$_3$BO$_3$ | 0.300 | g $L^{-1}$ |
| CoCl$_2$•6H$_2$O | 0.200 | g $L^{-1}$ |
| NiSO$_4$•6H$_2$O | 0.025 | g $L^{-1}$ |
| Na$_2$MoO$_4$•2H$_2$O | 0.030 | g $L^{-1}$ |
| CuSO$_4$•5H$_2$O | 0.015 | g $L^{-1}$ | pH adjusted to 2.0 ± 0.5 using 6N HCl

Two fermenters were filled with 1 kg of initial charge (see Table 13) containing glycerol as the carbon source at 14.77 g $kg^{-1}$ and were inoculated with 100 g of seed culture as described in the preceding paragraph. The OD$_{600}$ after inoculation was 0.2 AU/mL.

TABLE 13

Initial Charge for the batch phase (filter sterilized 0.2 µm)

| Component | Concentration | Unit |
| --- | --- | --- |
| Na$_2$HPO$_4$ | 0.37 | g $kg^{-1}$ |
| (NH$_4$)$_2$SO$_4$ | 5.47 | g $kg^{-1}$ |
| KH$_2$PO$_4$ | 0.55 | g $kg^{-1}$ |
| Nitrilotriacetic acid | 0.15 | g $kg^{-1}$ |
| NH$_4$ (Fe-II)SO$_4$•6H$_2$O | 0.05 | g $kg^{-1}$ |
| MgSO$_4$•7H$_2$O | 0.5 | g $kg^{-1}$ |
| CaCl$_2$•2H$_2$O | 0.01 | g $kg^{-1}$ |
| Trace metal solution (see Table 12A) | 10 | mL $kg^{-1}$ |
| Antifoam 204 | 0.5 | mL $kg^{-1}$ |

Following inoculation, both fermentations proceeded in batch mode with aerobic heterotrophic growth until stationary phase (there was enough carbon source in each to maintain batch growth for 24-48 h). Aerobic heterotrophic batch growth was monitored and once established the feeds were started in cell retention mode, the permeate being removed to maintain the hold-up of 1.1 kg.

Once in stationary phase both fermenters were put into chemostat mode with partial cell retention with permeate being removed to maintain a hold-up of 1.1 kg to achieve carbon-limited aerobic heterotrophic growth.

Both fermenters were fed by two separate feeds, mineral feed (see Table 14) plus 15 g/Kg of Glycerol at 100 g/h and a phosphate feed (see Table 15) at 20 g/h. The pH was adjusted by NH$_4$OH (10% w/w) and H2SO4 10% (v/v). The cell dilution rate was D=0.025 h−1.

TABLE 14

Sterile Mineral Feed supplied at 100 g h−1 (filter sterilized 0.2 µm)

| Component | Concentration | Unit |
| --- | --- | --- |
| Nitrilotriacetic acid | 0.15 | g $kg^{-1}$ |
| (NH$_4$)$_2$SO$_4$ | 3 | g $kg^{-1}$ |
| MgSO$_4$•7H$_2$O | 0.5 | g $kg^{-1}$ |
| CaCl$_2$•2H$_2$O | 0.01 | g $kg^{-1}$ |
| NH$_4$ (Fe-II)SO4•6H2O | 0.05 | g $kg^{-1}$ |
| Trace metal solution (see Table 12A) | 10 | mL $kg^{-1}$ |
| Antifoam 204 | 0.5 | mL $kg^{-1}$ |

TABLE 15

Sterile Phosphate Feed supplied at 20 g h−1 (filter sterilized 0.2 µm)

| Component | Concentration | Unit |
| --- | --- | --- |
| KH$_2$PO$_4$ | 3 | g $kg^{-1}$ |
| Na$_2$HPO$_4$ | 2 | g $kg^{-1}$ |

Samples for protein analysis and amino acid profiling were collected and analysed to give the relative % weight amino acids, AA (% WT of amino acid/% WT of total amino acid) on a dry weight basis, as shown in Table 16. Samples were analysed at the Experiment Station Chemical Laboratories at University of Missouri, Columbus, Mo. according to Code 0002 for the Amino Acid Profile and Code 0054 for the Crude Protein/Total Nitrogen (Kjeldahl).

TABLE 16

| Process | Units<br>% WT of AA/% WT of total AA<br>Strain<br>*Cupriavidus necator*<br>H16 ΔphaCAB<br>Feedstock<br>Glycerol<br>Continuous |
| --- | --- |
| Alanine | 9.88 |
| Arginine | 7.51 |
| Aspartic Acid | 9.64 |
| Cysteine | 0.80 |
| Glutamic Acid | 12.06 |
| Glycine | 6.24 |
| Histidine | 2.08 |
| Hydroxylysine | 0.01 |
| Hydroxyproline | 0.06 |
| Isoleucine | 4.51 |
| Lanthionine | 0.00 |
| Leucine | 8.57 |
| Lysine | 6.24 |
| Methionine | 2.59 |
| Ornithine | 0.04 |
| Phenylalanine | 4.59 |
| Proline | 4.33 |

TABLE 16-continued

| Process | Units<br>% WT of AA/% WT of total AA<br>Strain<br>*Cupriavidus necator*<br>H16 ΔphaCAB<br>Feedstock<br>Glycerol<br>Continuous |
|---|---|
| Serine | 3.58 |
| Taurine | 0.07 |
| Threonine | 4.90 |
| Tryptophan | 1.87 |
| Tyrosine | 3.32 |
| Valine | 7.10 |
| Total Amino Acids (WT %) | 72.08 |
| Crude Protein* | 88.80 |

W/W % = grams per 100 grams of sample.
Results are expressed on a dry weight basis.
*Kjeldahl crude protein = (% N) × 6.25

Example 8: Biomass Production Using Continuous Mode Fermentation with Fructose as Feedstock The strain used for this experiment was *Cupriavidus necator* H16 ΔphaCAB. Unlike the strain in Example 7, this strain had not been adapted to grow in glycerol by subculturing it in minimal medium with glycerol.

4×10 ml inoculum culture medium (see Table 12 in Example 7) plus fructose at 12 g L$^{-1}$ in a 50 mL sterile centrifuge tube was inoculated with a colony from a TSB plate and grown for 24 h at 30° C. and 220 rpm.

This preculture was used to inoculate 3×100 ml inoculum culture media (see Table 12 in Example 7) with fructose at 12 g L$^{-1}$ in 1 L flasks to an initial OD 600 nm of 0.2 followed by incubation for 11 h at 30° C. and 220 rpm to achieve a final OD 600 nm of ~2.2. Two×100 mL of these were monoseptically transferred into 1 L inoculum flasks ready for inoculation. Two 1.5-L stirred tank fermenters were filled with 1 kg of initial charge medium (Table 13 in Example 7) containing fructose at 13.83 g kg$^{-1}$ as carbon source and were inoculated with 100 g of seed culture as described supra. OD$_{600}$ after inoculation was 0.2 AU/mL.

Following inoculation, both fermentations proceeded in batch mode with aerobic heterotrophic growth until stationary phase (there was enough carbon source in each to maintain batch growth for 24-48 h). Aerobic heterotrophic batch growth was monitored and once established, the feeds were started in cell retention mode, the permeate being removed to maintain a hold-up of 1.1 kg.

Once in stationary phase, both fermenters were put into chemostat mode with partial cell retention with permeate being removed to maintain a hold-up of 1.1 kg to achieve carbon-limited aerobic heterotrophic growth.

Both fermenters were fed by two separate feeds, mineral feed (see Table 12A in Example 7) plus 14 g/Kg of fructose at 100 g/h and a phosphate feed (see Table 13 in Example 7) at 20 g/h. The pH was adjusted by NH$_4$OH (10% w/w) and H$_2$SO$_4$ 10% (v/v). The culture dilution rate was D=0.05 h$^{-1}$.

Samples for protein analysis and amino acid profiling were collected and analysed to give the relative % weight amino acids, AA (% WT of amino acid/% WT of total amino acid) amino acids on a dry weight basis, as shown in Table 17. Samples were analysed at the Experiment Station Chemical Laboratories at University of Missouri, Columbus, Mo. according to Code 0002 for the Amino Acid Profile and Code 0054 for the Crude Protein/Total Nitrogen (Kjeldahl).

TABLE 17

| Process | Units<br>% WT of AA/% WT of total AA<br>Strain<br>*Cupriavidus necator*<br>H16 ΔphaCAB<br>Feedstock<br>Fructose<br>Continuous |
|---|---|
| Alanine | 9.60 |
| Arginine | 7.70 |
| Aspartic Acid | 9.64 |
| Cysteine | 0.90 |
| Glutamic Acid | 11.95 |
| Glycine | 6.28 |
| Histidine | 2.18 |
| Hydroxylysine | 0.03 |
| Hydroxyproline | 0.04 |
| Isoleucine | 4.65 |
| Lanthionine | 0.00 |
| Leucine | 8.70 |
| Lysine | 6.32 |
| Methionine | 2.60 |
| Ornithine | 0.05 |
| Phenylalanine | 4.58 |
| Proline | 4.20 |
| Serine | 3.40 |
| Taurine | 0.05 |
| Threonine | 4.79 |
| Tryptophan | 1.63 |
| Tyrosine | 3.47 |
| Valine | 7.23 |
| Total Amino Acids (WT %) | 73.54 |
| Crude Protein* | 88.58 |

W/W % = grams per 100 grams of sample.
Results are expressed on a dry weight basis.
*Kjeldahl crude protein = (% N) × 6.25

Example 9: Single Cell Protein Production from Gas Fermentation

Samples of the *Cupriavidus necator* H16 ΔphaCAB strain were grown chemoautolithotrophically during continuous carbon-limited gas (H$_2$, CO$_2$ and air) fermentation.

Total amino acid content and amino acid profiles were analyzed from these samples and a comparison was made with those samples analyzed from heterophically grown cells on clarified thin stillage and other glycerol media.

Glycerol vials of 1 mL strains of the *Cupriavidus necator* H16 ΔphaCAB strain which had been adapted to grow in glycerol were used to inoculate a 0.25 L baffled flask containing 25 mL of inoculum culture medium (Table 12 from Example 7) plus glycerol at 18 g L. The culture was incubated for 3-4 days (30° C., 220 rpm) to a final OD600- 2.2 AU/mL. The expected growth rate was 0.08 h$^{-1}$. 10 mL of the culture was then transferred into two 1 L baffled flasks containing 90 mL of inoculum culture medium (Table 12 from Example 7) plus glycerol at 18 g L$^{-1}$. These cultures were incubated for 20-24 h (30° C., 220 rpm) to a cell density of ~1.6-2.5 AU/mL (~0.75 g/L), with the culture still in the exponential phase. The expected growth rate was 0.12 h$^{-1}$.

A 2 L stirred-tank bioreactor fitted with two Rushton turbines and cell recycle cross flow membrane system was inoculated to a target OD600 of ~0.2 AU/mL (0.1 g/L) with 200 mL of exponentially growing *Cupriavidus necator* H16 ΔphaCAB inoculum culture from two inoculum flasks into 1.3 L of initial charge medium (Table 13 from Example 7) containing glycerol at 14 g kg$^{-1}$ as a carbon source.

Following inoculation, the fermentations proceeded in batch mode with aerobic heterotrophic growth until stationary phase (depletion of glycerol). The total gas feed flow (aeration feed rate) was initially set to 0.050 SLPM and agitation rate cascaded to a DO controller to achieve a set point of 30% DO saturation until the initial maximum agitation set point of 900 rpm was reached.

When the culture entered stationary phase, the $H_2$ and $CO_2$ feeds were initiated, and autotrophic growth was established. The separate feed gas flow rates ($H_2$, $CO_2$ and air) were controlled by a combination of operator-set flow ratios and cascade control. The $CO_2$ feed ratio ($CO_2$ feed flow to total gas feed flow) was adjusted to achieve the target $CO_2\%$ v/v. The $O_2$ feed ratio (air feed flow to total gas feed flow) was manually adjusted to meet the dissolved oxygen target of % 1-10% (sat). The total gas feed flow (air+$H_2CO_2$) was cascaded to an off-gas $O_2$ concentration controller having an initial set point of 3% v/v $O_2$ and a maximum set point of 3.5% v/v $O_2$ to keep below the limiting oxygen concentration. The agitation set point was manually increased to and maintained at a fixed 950 rpm (maximum allowable sustained speed without concern about agitator motor damage) for the duration of the experiment.

The mineral and phosphate feeds were initiated, and $CO_2$ feed was controlled to 4% v/v of the total gas feed ($CO_2$, $H_2$ and air). There was 100% cell retention and the hold up (total system volume) was maintained at 1.5 L by an out flow of permeate from the cross-flow membrane. The off-gas concentration set point also increased from 3 to 3.5% v/v. With mineral feed set to 0.148 L h$^{-1}$ and phosphate feed set to 0.045 L h$^{-1}$ the culture bleed (waste) was initiated; in partial cell retention mode. In this mode permeate flow rate was fixed while the bleed flow rate was used to control the reactor hold-up level. The cell dilution rate was initially D=0.042 h$^{-1}$ and $CO_2$ in total gas feed was controlled to 4% v/v.

With feed rates, permeate and bleed rates established the $CO_2\%$ in the total gas feed was reduced from 4 to 2% v/v to achieve carbon limitation. Mineral feed rate was first increased to 0.163 L h$^{-1}$, adjusted to 0.158 L h$^{-1}$. The phosphate feed was also adjusted to 0.036 L h$^{-1}$. The dilution rate, D, was increased to 0.05 h$^{-1}$ by adjustment of the permeate rate. Whole culture samples were taken for freeze drying and protein content and amino acid analysis; an initial sample was taken without ice and then a further sample was taken on ice from the culture bleed line.

All gases were purged from the fermentation system with 100% $N_2$ at 0.5 SLPM.

It would be difficult to establish a steady state in this system as the gas flow rates were not constant. The fermentation inlet and outlet gases were monitored online continuously by micro-GC. Biomass (g L$^{-1}$) Phosphoric acid (g L$^{-1}$) and Glycerol (g L$^{-1}$) were monitored offline.

Table 18 shows a summary of the fermentation parameter set points for cell retention mode.

TABLE 18

| Parameter | Autotrophic Steady state (continuous mode partial cell retention) 115.92$^{-1}$70.16 h C-limited [2% CO2 low feed rate] |
|---|---|
| Temperature set point | 30 |
| Agitation set point | 950 |
| pH (mean pH reading) | 6.54 |
| Total system volume | 1.5 |
| Off gas $O_2$ set point (mean reading) | 3.84 |

TABLE 18-continued

| Parameter | Autotrophic Steady state (continuous mode partial cell retention) 115.92$^{-1}$70.16 h C-limited [2% CO2 low feed rate] |
|---|---|
| Dissolved $O_2$ set point (mean reading) | 2.38 |
| Air feed flow rate (MFC set point) min-max (mean) | 0.147 |
| $CO_2$ feed flow rate (MFC set point) min-max (mean) | 0.00803 |
| $CO_2$ % in feed min-max (mean) | 2.2 |
| $H_2$ feed flow rate (MFC set point) min-max (mean) | 0.313 |
| $H_2$ % in feed min-max (mean) | 62.46 |
| Mineral feed rate flow rate settings | 0.163 @ 116.4 h, 0.158 @ 123.12 h |
| Phosphate feed rate flow rate settings | 0.045 @ 116.4 h, 0.0358 @ 123.12 h |
| Permeate flow rate[2] flow rate settings | 0.100 @ 116.4 h, 0.1208@ 123.12, 0.150 @ 138 h |
| D (Dwaste) dilution rate[3] | 0.0417 @ 92.16 h, 0.05 @ 123.12 h |
| $CO_2$ feed ratio ($CO_2/(CO_2 + H_2 +$ Air))[4] min-max (mean) | 0.0171 |
| $O_2$ feed ratio (Air/($CO_2 + H_2 +$ Air))[5] min-max (mean) | 0.313 |
| Total feed Gas flow rate (MFC set point) min-max (mean) | 0.467 |
| Cascade | Total feed gas flow cascaded against off-gas $O_2$ % v/v |

The relative % weight amino acids (% WT of amino acid/% WT of total amino acid) amino acids on a dry weight basis is shown in Table 19. Samples were analysed at the Experiment Station Chemical Laboratories at University of Missouri, Columbus, Mo. according to Code 0002 for the Amino Acid Profile and Code 0054 for the Crude Protein/Total Nitrogen (Kjeldahl).

TABLE 19

| Process | Units<br>% WT of AA/% WT of total AA<br>Strain<br>*Cupriavidus necator*<br>H16 ΔphaCAB<br>Feedstock<br>CO2/H2<br>Continuous |
|---|---|
| Alanine | 8.64 |
| Arginine | 8.22 |
| Aspartic Acid | 10.01 |
| Cysteine | 0.93 |
| Glutamic Acid | 11.47 |
| Glycine | 5.91 |
| Histidine | 2.51 |
| Hydroxylysine | 0.02 |
| Hydroxyproline | 0.04 |
| Isoleucine | 4.92 |
| Lanthionine | 0.00 |
| Leucine | 8.70 |
| Lysine | 5.52 |
| Methionine | 2.96 |
| Ornithine | 0.06 |
| Phenylalanine | 4.97 |
| Proline | 4.22 |
| Serine | 3.34 |
| Taurine | 0.04 |
| Threonine | 5.04 |
| Tryptophan | 1.59 |
| Tyrosine | 3.74 |
| Valine | 7.14 |
| Total Amino Acids (WT %) | 81.34 |
| Crude Protein* | 93.45 |

W/W % = grains per 100 grams of sample.
Results are expressed on a dry weight basis.
*Kjeldahl crude protein = (% N) x 6.25

Example 10: Lab-Scale Production of Single-Cell Protein of *Cupriavidus necator* from Used Cooking Oil

*C. necator* can utilize fatty acids and oils as carbon and energy sources under aerobic conditions (Verlinden et al. 2011 AMB Express. 11; Taniguchi I. et al. 2003 Microbial production of poly(hydroxyalkanoates) from waste edible oils, 5: pp. 545). An economically attractive stream is used cooking oil (Nielsen et al. 2017 Microbial Biotechnology 10:6 pp. 1338-1352 doi: 10.1111/1751-7915.12776) and it has been demonstrated that *C. necator* could efficiently use these streams to make PHB (Obruca et al., 2014 Appl. Microbiol. Biotechnol. 98: pp. 5883-5890).

A study was therefore carried out to assess the feasibility of using *C. necator* to produce single-cell protein (SCP) with used cooking oil as fermentation feedstock. Batch and fed-batch fermentation conditions were tested to obtain enough biomass for protein content and amino acid profile analysis.

The *C. necator* H16 ΔphaCAB strain as used in previous Examples was adapted to grow in glycerol.

200 μL of concentrated cells from a culture of the *C. necator* H16 ΔphaCAB strain were used to inoculate 10 mL of inoculum culture medium plus glycerol at 18 g L$^{-1}$ (see Table 12 in Example 7) in 50 mL sterile tubes and incubated at 30° C., 220 rpm for 24 h. This culture was used to inoculate different tubes with 10 mL of fresh medium with glycerol with an initial OD600 of 0.2 AU/mL. The tubes were incubated at 30° C., 220 rpm for 24 h to an approximate OD600 of 2 AU/mL.

The preculture tubes were used to inoculate 100 mL of fresh medium with glycerol in 1 L flasks to an initial OD600 of 0.2 AU/mL, the flasks were grown for approx. 40 h to a final OD600 of 2 AU/mL, at which point the fermenters were inoculated with a ratio 1:10 to an initial OD600 of 0.2 AU/mL. The experiments were carried out in fermentation units, each unit was loaded with 700 g of initial charge medium plus glycerol at 14.77 g kg$^{-1}$ as carbon source (see Table 13 in Example 7) and seeded with 70 g of inoculum.

In all cases the temperature control was set to 30° C., and pH was measured and controlled at 6.6±0.05 with filter-sterilized (0.2 μm) NH$_3$ 10% w/w and H2SO4 10% v/v. During the fermentation process, dissolved oxygen (% DOsat) was measure and controlled above 30% DOsat; being 100% DOsat the dissolved oxygen concentration at equilibrium with air at 1 bar (absolute pressure). Dissolved oxygen control was achieved by cascading the stirring speed between 582 rpm and 1500 rpm and airflow rate was maintained constant at 0.390 SLPM.

The end of the batch phase was marked by a spike in % DOsat and sudden decrease of % CO2 off-gas. All cultures were left in periods of starvation to ensure full initial C-source consumption. The fed-batch phase was run for an operational window of 6 h, the operation was designed to stop when the overall volume in the fermenter was around 620 g. At that point the fermenters were harvested to obtain samples for amino acid analysis. In all cases, the fed-batch was started by feeding simultaneously 20 g/h of mineral feed and 1 g/h of autoclaved used cooking oil; the samples of fed-batch operation were taken 30 min after stopping both feeds simultaneously.

240 mL samples were obtained at the end of the batch and fed-batch phases. The samples were centrifuged at 12000 rpm, 4° C., 10 min in 50 mL sterile tubes. The cell pellets were stored at −20° C. for 24 h, then lyophilized for approx. 48 h at a pressure lower than 120 Torr with condensate trap working at −50° C. The dry solids were analyzed to determine the amino acid and protein content in dry biomass.

In both batch and fed-batch operation, the amino acid profile changed with less than 30% variability across the different amino acids measured. The data is indicative of the C-source and operation mode playing a role in determining the amino acid profile.

Results show that *C. necator* uses cooking oil as sole carbon source with a calculated biomass yield of 0.8 gCDW/g oil, the specific growth rate of 0.27 l/h and biomass productivity of approximately 1 gCDW/kg/h.

After analyzing the amino acid profile and protein content, it was possible to observe a difference between operation modes. The experimental evidence suggests that the protein content decreases in fed-batch operation, the protein content as the sum of all amino acids in (g amino acids/g CDW) varies between 35% and 47%. Batch operations seem to yield consistently biomass with 45% protein content, comparable to the standard batch in thin stillage used in fish trials. On the other hand, fed-batch operations yield biomass with 37% protein content.

The relative % weight amino acids (% WT of amino acid/% WT of total amino acid) on a dry weight basis is shown in Table 20. Samples were analysed at the Experiment Station Chemical Laboratories at University of Missouri, Columbus, Mo. according to Code 0002 for the Amino Acid Profile and Code 0054 for the Crude Protein/Total Nitrogen (Kjeldahl).

TABLE 20

| Process | Units<br>% WT of AA/% WT of total AA<br>Strain<br>*C. necator*<br>H16 ΔphaCAB<br>Feedstock<br>Used Cooking Oil<br>Fed-Batch |
|---|---|
| Alanine | 9.71 |
| Arginine | 7.52 |
| Aspartic Acid | 9.57 |
| Cysteine | 0.75 |
| Glutamic Acid | 12.30 |
| Glycine | 6.48 |
| Histidine | 2.05 |
| Hydroxylysine | 0.05 |
| Hydroxyproline | 0.10 |
| Isoleucine | 4.89 |
| Lanthionine | 0.00 |
| Leucine | 8.66 |
| Lysine | 6.43 |
| Methionine | 2.71 |
| Ornithine | 0.07 |
| Phenylalanine | 4.68 |
| Proline | 4.15 |
| Serine | 3.40 |
| Taurine | 0.05 |
| Threonine | 4.94 |
| Tryptophan | 1.08 |
| Tyrosine | 3.15 |
| Valine | 7.27 |
| Total Amino Acids (WT %) | 60.07 |
| Crude Protein* | 78.12 |

W/W % = grams per 100 grams of sample.
Results are expressed on a dry weight basis.
*Kjeldahl crude protein = (% N) × 6.25

Example 11: Use of Enzymatic Pretreatment (or Co-Treatment) to Increase the Conversion of Complex Carbohydrates or Proteins to SCP A *Cupriavidus necator* H16 ΔphaCAB strain with a further deletion (ΔH16_A0006-9) made to increase transformation efficiency (as described in published application US20180100160, which is hereby incorporated by reference in its entirety) was adapted to grow using glucose as the sole source of carbon by extended incubation in minimal medium containing glucose.

Concentrated cells from the *Cupriavidus necator* H16 ΔphaCAB ΔH16_A0006-9 strain were used to inoculate culture medium (see Table 12 in Example 7) containing glucose at 12 g L$^{-1}$ and incubated at 30° C. with shaking for 48 h.

These pre-cultures were each transferred to a 50 mL sterile tube and centrifuged to pellet the cells. The supernatant was removed, and the pellet washed in 20 mL of fresh culture medium (see Table 12 in Example 7) with no additional carbon source. The pellet was finally resuspended in fresh culture medium (see Table 12 in Example 7) with no carbon sources or ddH$_2$O and OD600 measured.

*Cupriavidus necator* H16 ΔphaCAB ΔH16_A 0006-9 strains when grown on complex carbohydrate-based media alone or when pretreated with enzymes to break down the complex carbohydrate were studied. Carbohydrates tested are shown in Table 15.

Carbohydrates—Untreated:

2× inoculum culture medium (Table 12 in Example 7)+2% carbohydrates (pH adjusted and filtered through 0.2 μm membrane) were incubated overnight at 30° C. at 220 rpm then inoculated to approximately OD600 0.4. ½ final volume was aliquoted in vessel of choice and sterile ddH$_2$O was added to final volume. Growth was monitored by OD600. Conditions were set up as triplicates and the error was calculated as 2×STDEV. Carbohydrates are as listed in Table 22.

Carbohydrates—Enzyme Treatment:

2× fresh culture medium+2% carbohydrates+enzymes (as shown in Table 14) was pH adjusted to 6.6, filtered through 0.2 μm membrane and incubated overnight at 30° C., 220 rpm. Starch and Pectin were firstly resuspended directly in approximately 500 μL of concentrated enzyme and then 2× fresh culture medium was added to adjust to the required final volume. 250 μL of this mixture was aliquoted into a 96 deep well square plate. The inoculum was resuspended in sterile ddH$_2$O to approximately OD600 0.4 and added to the mixture in the culture plate. Growth was monitored by OD600. Conditions were set up as triplicates and the error was calculated as 2×STDEV.S

TABLE 21

| Enzymes tested | | |
|---|---|---|
| Enzyme | Concentration | Range tested |
| Maltase (α-Glucosidase) | >=100 units/mg protein | 15-90 U (For Maltose), 25-200 U (For Starch) |
| Invertase (β-D-Fructofuranosidase) | 200-300 units/mg | 15-50 U |
| Lactase (β-Galactosidase) | >2600 units/gr | 2-20 μl |
| α-Amylase (1,4-α-D-Glucan-glucanohydrolase) | | 1-7 μl (For Maltose), 10-500 μl (For Starch) |
| Amyloglucosidase (1,4-α-D-Glucan glucohydrolase) | >260 units/mL | 15-90 U (For Maltose), 60-500 U (For Starch) |
| Amyloglucosidase (1,4-α-D-Glucan glucohydrolase) | 30-60 units/mg | 15-50 U (For Maltose), 50-300 U (For Starch) |
| Proteinase K | 800 units/mL | |

Results for the studies using untreated carbohydrates and carbohydrates+enzyme treatment are shown below in Table 22.

TABLE 22

| Sugar | Enzyme | Concentration | OD600 72 hr | OD600 96 hr |
|---|---|---|---|---|
| Glycerol | None | 1% | 0.17 | 0.43 |
| Glucose | None | 2% | 0.78 | |
| Maltose | None | 1% | 0.16 | 0.18 |
| Maltose | 100 μL Amyloglucosidase | 1% | 1.24 | 1.41 |
| Starch | None | 1% | 0.17 | 0.17 |
| Starch | 100 μL Amylase + 100 μL Amyloglucosidase | 1% | 2.03 | 2.22 |
| Sucrose | None | 1% | 0.16 | 0.17 |
| Sucrose | 15 Units Invertase | 1% | 0.68 | 0.82 |
| Lactose | None | 1% | 0.16 | 0.17 |
| Lactose | 2 μL Lactase | 1% | 0.53 | 0.98 |
| Raffinose | None | 1% | 0.16 | 0.18 |
| Raffinose | 2 μL Lactase + 15 Unit Invertase | 1% | 1.01 | 1.12 |
| No Carbon Source | None | | 0.16 | 0.17 |
| Blank | None | | 0.07 | 0.07 |

Data showed that *Cupriavidus necator* H16 ΔphaCAB ΔH16_A0006-9 was unable to utilize untreated complex carbohydrates (di- and oligosaccharides) as a sole carbon source. However, when grown on complex carbohydrates which had been subject to enzymatic hydrolysis to release monosaccharides, growth was observed under certain conditions.

An investigation was then undertaken to study *Cupriavidus necator* H16 ΔphaCAB ΔH16_A0006-9 when grown on protein-based substrates with and without protease treatment. A 96-well plate was used to measure growth in the following media containing proteins or amino acids as the sole source of carbon at the stated concentration: BSA 1% and 2%, casamino acids (i.e. acid casein hydrolysate) 1% and 2%, tryptone (i.e. casein enzymatic digest) 1% and 2%, aspartic acid 0.25% and 0.125%, glutamine 0.5% and 1%, lysine 1% and 2% and D-Fructose (1%) or D-glucose 1% as a positive control. Carbon source additions were made to sterile mineral salts medium and the pH was adjusted to 6.6. Each well of the plate contained 100 μL of medium and was inoculated with *Cupriavidus necator* H16 ΔphaCAB ΔH16_A0006-9 at an initial O$_{D600}$ (measured with the plate reader) of ~0.1.

A 10 mL Falcon tube format was used to measure growth in medium containing 2% BSA, pre-treated with proteinase K. Specifically, a filter-sterilised solution of 2% BSA was incubated for 24 h with proteinase K (100 μL proteinase K per 2 mL BSA solution, pH 6.6), was inoculated (staring OD$_{600}$=0.1) with a stationary-phase culture of *C. necator* H16 ΔphaCAB ΔH16_A0006-9 grown on fructose 1%. A control containing non-pre-treated BSA was also prepared. The blank was inoculum culture media (see Table 12 of Example 7) plus 2% BSA, with no inoculum. All samples were prepared in triplicates.

Figure 2:
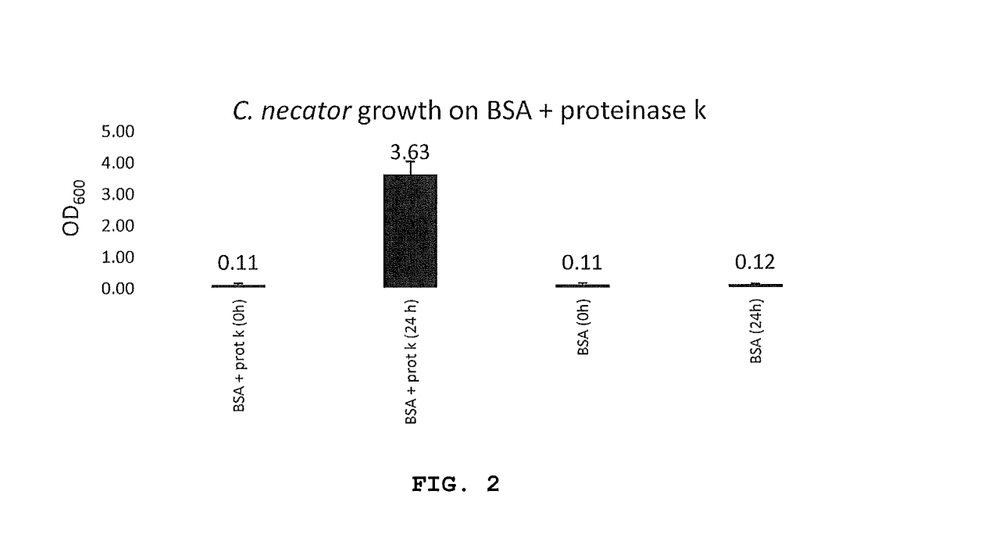
FIG. 2 is a graph showing the growth of *Cupriavidus necator* H16 ΔphaCAB ΔH16_A0006-9 strain increasing when protein-rich medium BSA is pre-treated with proteinase K.

As shown in FIG. 2, the growth of *Cupriavidus necator* H16 ΔphaCAB ΔH16_A0006-9 strain increased when the protein-rich medium BSA was pre-treated with proteinase K.

What is claimed is:

1. A feed or feed additive comprising at least 10% up to 30% of a *Cupriavidus necator* H16 strain generated to attenuate or eliminate poly(3-hydroxybutyrate)(PHB) production using allele exchange (ΔphaCAB) and poultry meal.

2. The feed or feed additive of claim 1 which is for ruminant and non-ruminant animals or for aquaculture.

3. A method for improving survivability of a livestock or aquaculture animal, said method comprising feeding the animal the feed or feed additive of claim 1.

4. A method for decreasing waste-products from commercial operations, said method comprising:

growing an organism originally capable of producing poly(3-hydroxybutyrate)(PHB) in the waste-products, wherein the organism has attenuated and/or no PHB production, wherein the organism does not comprise an exogenous nucleic acid, wherein the organism has at least one modification of one or more of the phaCAB operon enzymes excluding a phasin modification, and wherein the organism is *Cupriavidus necator*;

harvesting the organism; and incorporating the harvested organism into the feed or feed additive of claim 1.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
atcgaagaga agcaggacga                                               20

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
aacggcaggt atatgtgatg g                                             21
```